United States Patent [19]

D'Hinterland et al.

[11] Patent Number: 4,937,327

[45] Date of Patent: Jun. 26, 1990

[54] DERIVATIVE OF D.25, PROCESS FOR ITS PREPARATION, ITS USE AS AN IMMUNOSTIMULANT, AND PHARMACEUTICAL COMPOSITIONS CONTAINING THE DERIVATIVE

[75] Inventors: Lucien D. D'Hinterland; Gérard Normier; Anne-Marie Pinel, all of Castres, France

[73] Assignee: Pierre Fabre Medicament, Paris, France

[21] Appl. No.: 185,104

[22] Filed: Apr. 22, 1988

[30] Foreign Application Priority Data

Apr. 22, 1987 [FR] France ............................ 87 05690

[51] Int. Cl.$^5$ .................... A61K 31/415; A61K 39.39; A61K 45/05; C08B 37/00
[52] U.S. Cl. ....................................... 536/1.1; 536/53; 424/92; 514/889
[58] Field of Search .................. 536/1.1, 53; 514/889; 424/92

[56] References Cited

U.S. PATENT DOCUMENTS

| | | | |
|---|---|---|---|
| 4,476,119 | 10/1984 | della Valle et al. | 514/25 |
| 4,501,693 | 2/1985 | D'Hintenland et al. | 435/70 |
| 4,593,091 | 6/1986 | della Valle et al. | 514/54 |
| 4,713,374 | 12/1987 | della Valle et al. | 536/53 |
| 4,716,223 | 12/1987 | della Valle et al. | 536/53 |
| 4,734,403 | 3/1988 | D'Hintenland et al. | 536/1.1 |
| 4,755,381 | 7/1988 | Coyz | 424/92 |
| 4,783,527 | 11/1988 | Falkowski et al. | 536/53 |

FOREIGN PATENT DOCUMENTS

180564 5/1986 European Pat. Off.

*Primary Examiner*—Ronald W. Griffin
*Attorney, Agent, or Firm*—Dressler, Goldsmith, Shore, Sutker & Milnamow, Ltd.

[57] ABSTRACT

The present invention relates to a polysaccharide derivative, which is a derivative of D.25 in which the galactofuranose (Gal$f$) residues of the linear polysaccharide chain have been converted at least partly to arabinose.

It also relates to the process for its preparation, to its use as an immunostimulant, and to pharmaceutical compositions containing the derivative.

11 Claims, No Drawings

DERIVATIVE OF D.25, PROCESS FOR ITS PREPARATION, ITS USE AS AN IMMUNOSTIMULANT, AND PHARMACEUTICAL COMPOSITIONS CONTAINING THE DERIVATIVE

The present invention relates to novel compounds derived from D.25, to the process for their preparation and to the pharmaceutical compositions in which they are present.

The product called D.25 is the polysaccharide extracted from bacterial membrane proteoglycanes, comprising essentially galactose units and having a molecular weight of 30±10 KD. This polysaccharide has been described in detail in French Patent No. 84/13,844 filed on 10th September 1984. This polysaccharide possesses immunostimulant properties, especially in respect of the induction of endogenous interferon and the activation of NK (Natural Killer) cells. This polysaccharide is preferentially isolated from a non-capsulated and non-pathogenic strain of *Klebsiella pneumoniae* biotype a, deposited in the National Collection of the Pasteur Institute under number 145.I.IP.

The present invention relates to compounds derived from D.25, in which at least a part of the galactofuranose residues (Gal$_f$) of the linear polysaccharide chain of the D.25 have been converted to arabinose without any other modification of the initial product. In these compounds, the galactopyranose residues (Gal$_p$) are preferably preserved.

Among these compounds, one is particularly interesting. This is the compound in which all the galactofuranose residues of the linear polysaccharide chain have been converted to arabinose and which is defined by the following monomer:

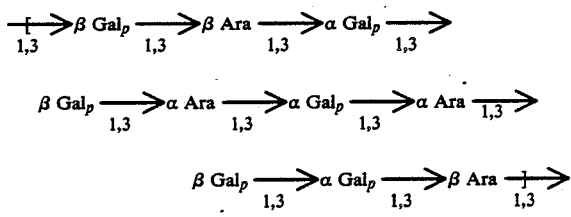

in which Gal$_p$ is galactopyranose ($\alpha$ and $\beta$ forms) and Ara is arabinose ($\alpha$ and $\beta$ forms).

The invention also relates to the derivatives of the above compounds, namely, in particular:
- semisynthetic derivatives
- labeled derivatives and
- conjugated derivatives.

Among the semisynthetic derivatives, there may be mentioned the amides, esters, ethers, salts or quaternary ammonium derivatives with acids, amines, amides or alcohols.

The derivatives of the compounds according to the present invention can also be compounds labeled by any suitable method, for example by means of radioactive elements such as I$^{125}$ or Tc$^{99}$, or by using fluorescent or magnetic compounds. Thanks to this type of labeling, the products in question can be detected in vivo or ex vivo.

The derivatives of the compounds according to the invention can also be conjugated with chemical compounds capable of improving their activity or which can bring them close to particular sites, especially of the immune system, so as to enable them to improve the activity of the conjugated chemical product.

A process for obtaining the compounds of the present invention comprises subjecting D.25 to a periodate oxidation followed by a reduction.

The oxidation is preferably carried out with the aid of sodium metaperiodate. The reduction can be carried out with the aid of NaBH$_4$, optionally used in excess.

The derivatives of the compounds can be obtained by known methods, namely a labeling method or a conjugation method.

The compounds according to the invention and their derivatives exhibit noteworthy immunostimulant properties and an absence of cytotoxicity. It is for this reason that the invention also relates to the use of the compounds and of the derivatives as an immunostimulant as well as to pharmaceutical compositions containing at least one compound or one derivative according to the present invention.

The compounds and above all the labeled derivatives according to the invention can also be used for diagnostics, in particular for detecting certain elements of the immune system.

Other characteristics and advantages of the present invention will be clear on reading the detailed description which now follows.

EXAMPLE 1

Isolation of the crude membrane proteoglycane.

The biomass of the strain of *Klebsiella pneumoniae* 145.I.IP is dispersed in ice-cold Tris-HCl buffer (10 mM, pH 7.0) containing NaCl (0.15M) and is then subjected to mechanical grinding intended to break the cell walls. The bacterial lysate is clarified by continuous centrifuging at 15,000 g and the supernatant liquor is collected. The latter is treated by adding acetic acid, in the cold, until pH 4.2 is reached, so as to remove the impurities (nucleic acids and heavy proteins) by precipitation. The precipitate of impurities is removed by continuous centrifuging at 15,000 g. The limpid supernatant liquor is collected and then neutralized with NaOH.

The solution is then dialyzed, and is thereafter concentrated by ultrafiltration on a membrane with a cutoff at 10,000 Daltons.

The concentrated solution obtained at this stage corresponds to the crude membrane proteoglycane.

EXAMPLE 2

Isolation of the crude polysaccharide fraction.

This consists of a controlled alkaline hydrolysis intended to depolymerize the crude membrane proteoglycane to liberate the polysaccharide fraction. To the concentrated and dialyzed solution of crude membrane proteoglycane obtained above is added NaOH to give a final NaOH concentration of 0.5M. Thereafter hydrolysis is carried out for 1 hour at 56° C. After rapid cooling, the solution is neutralized with HCl.

The neutralized solution is clarified with filtration on a filter press and then concentrated by ultrafiltration on a membrane with a cutoff at 10,000 Daltons.

EXAMPLE 3

Purification of the polysaccharide fraction.

The concentrate obtained in the preceding example is subjected to a first enzymatic treatment with the lysozyme, intended to destroy the mureine residues which may persist during the preparation. The hydrolysis is carried out for 2 hours at ambient temperature in a Tris-HCl buffer (10 mM, pH 8.0) containing EDTA, Na$_2$ (4 mM) and 0.1 mg/ml of lysozyme.

After the action of the lysozyme, the contaminating proteins are removed by proteolysis under the following conditions: the pH of the solution is adjusted to 7.0 and 0.1 mg/ml of proteinase K is then added. The incubation is continued for 2 hours at 37° C., with stirring.

The polysaccharide is then isolated by precipitation with alcohol. Three volumes of ethyl alcohol are added at ambient temperature. After 30 minutes' stirring, the precipitate is collected by filtration. It is redissolved in distilled water and the solution is filtered over a membrane of porosity 0.45 μm.

The residual contaminants of the polysaccharide, originating from the enzymatic hydrolyses, are removed by molecular sieve chromatography on a Pharmacia industrial column with SEPHACRYL S200 HR gel. The volume of sample deposited represents 5% of the gel volume. Elution is carried out with distilled water at a linear flow rate of 5 cm/hour.

The purified polysaccharide peak, detected by continuous measurement of the refractive index, is collected and concentrated by ultrafiltration on a membrane with a cutoff at 10,000 Daltons, to 1/5 of the initial volume.

The concentrated solution obtained at this stage corresponds to the purified polysaccharide D.25.

EXAMPLE 4

Preparation of the novel polysaccharide.

The preceding solution is diluted so as to give 20 g of polysaccharide per liter of solution. 0.1 M sodium acetate is then added and the pH is adjusted to 3.8.

Thereafter, 15 g of sodium metaperiodate per liter of solution are added, after which stirring is continued for 48 hours in the dark, at a temperature of 15° C.

The excess metaperiodate is then removed by precipitation with barium hydroxide, in the form of a concentrated solution added gradually, with stirring, until the precipitation has ended. The precipitate thus formed is removed by simple filtration.

To the above filtrate are then added 21.6 g of NaBH$_4$, after which the mixture is left to react for 18 hours at ambient temperature. The excess NaBH$_4$ is then destroyed by adding acetic acid until the mixture is neutral.

The solution obtained is dialyzed, concentrated on a membrane with a cutoff at 10,000 Daltons and then lyophilized. The lyophilisate thus obtained, constitutes the novel D.25 derivative of the present invention.

EXAMPLE 5

Checking for absence of cytotoxicity.

The cytotoxicity is measured by in vitro incubation of various concentrations of the derivative of the present invention in a culture of YAC-1 cells labeled with $^{51}$Cr. After 4 hours' incubation, the yield of $^{51}$Cr liberated by the lysis of the cells is measured in the supernatant liquor. The results are expressed in terms of the percentage of cells lysed in comparison with a reference culture.

The spontaneous lysis in the reference culture is about 5%.

The results are reported in Table I below.

TABLE I

| Concentration in μg/ml | % of cell lysis |
| --- | --- |
| 0.05 | −0.2 |
| 0.1 | 1.0 |
| 0.5 | 0.3 |
| 1.0 | −1.0 |
| 5.0 | 0.3 |
| 10.0 | −0.4 |
| 50.0 | −0.1 |
| 100.0 | −1.3 |

The results show clearly that the product is completely devoid of cytotoxicity.

EXAMPLE 6

Activation of the NK cells in vitro.

Effector cells (mouse spleen cells) are preincubated for 6 hours in an RPMI-1640 medium containing 5% of calf fetus serum with various concentrations of the derivative to be tested.

The NK activity is measured on 10,000 YAC-1 target cells labeled with $^{51}$Cr in each well, with a ratio of effector cells/target cells of 100/1.

After 4 hours' incubation, the amount of $^{51}$Cr liberated into the supernatant liquor by lysis of the cells is measured with a gamma counter.

The results are given in Table II below.

TABLE II

| Concentration in μg/ml | % lysis of the YAC-1 target cells |
| --- | --- |
| 0-reference | 18.4 |
| 0.1 | 21.6 |
| 1.0 | 31.6 |
| 10 | 47.4 |
| 100 | 40.8 |

The results confirm the very high stimulant power of the derivative on the activity of the NK cells "in vitro".

EXAMPLE 7:

Activation of the NK cells "in vitro" in the mouse. Comparison with polysaccharide D.25.

CBA/H mice aged 6 to 8 weeks are given an intraperitoneal injection of 100 μg of the derivative of the present invention one day or three days before measuring the activity of their spleen NK cells.

The NK activity is then measured as above in the "in vitro" test.

The results are shown in Table III below.

TABLE III

| | % lysis of the target cells | |
| --- | --- | --- |
| Product injected | on Day + 1 | on Day + 3 |
| PBS-reference | 25.2 | 18.2 |
| D.25 (100 μg) | 20.0 | 22.0 |
| PS derivative (100 μg) | 32.6 | 26.8 |

The results presented in the table show that the novel polysaccharide has a stimulating capacity for NK cells which is greater than that of D.25.

This activity manifests itself from the first day after injection and continues to Day +3 while, under the same conditions, the activity of D.25 only appears on Day +3.

We claim:

1. A polysaccharide compound selected from the compounds derived from D.25 in which the galactofuranose residues (Gal$_f$) of the linear polysaccharide chain have been converted at least partly to arabinose, and the derivatives of these compounds.

2. The polysaccharide compound as claimed in claim 1, which is a derivative containing at least one sequence:

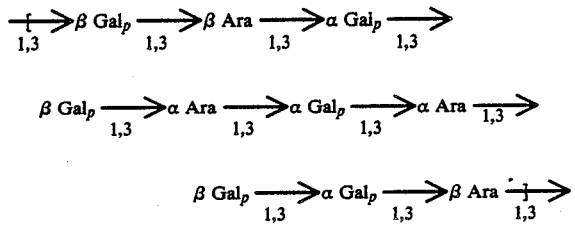

in which Gal$_p$ is galactopyranose (in the $\alpha$ and $\beta$ forms) and Ara is arabinose (in the $\alpha$ and $\beta$ forms).

3. The polysaccharide compound as claimed in claim 1 which is a derivative selected from the amides, esters, ethers, salts or quaternary ammonium derivatives with an amine, an amide, an acid or an alcohol.

4. The compound as claimed in any of claims 1, 2 or 3, which is a labeled compound.

5. The compound as claimed in any of claims 1, 2 or 3, which is a compound conjugated with a chemical compound.

6. A process for obtaining a compound as claimed in claim 1, which comprises
   (a) subjecting D.25 to a periodate oxidation and
   (b) subjecting the compound resulting from (a) to a reduction.

7. The process as claimed in claim 6, wherein the said periodate oxidation is performed with a metaperiodate, used in excess.

8. The process as claimed in claim 7, wherein sodium metaperiodate is used.

9. The process as claimed in any of claims 6, 7, or 8 wherein said reduction is performed with NaBH$_4$.

10. A pharmaceutical composition which comprises a pharmaceutically acceptable carrier or diluent and, by way of the active principle, at least one compound claimed in any of claims 1, 2 or 3, or its derivatives.

11. The process as claimed in claim 9 wherein said NaBH$_4$ is present during said reduction in an amount in excess of what is required for said reduction.

* * * * *